United States Patent [19]

Demler et al.

[11] 4,324,926
[45] Apr. 13, 1982

[54] PROCESS FOR THE PURIFICATION OF 4,4' DIHYDROXYDIPHENYL

[75] Inventors: Walter R. Demler, Hamburg; Krishen L. Nagpal, Williamsville; Richard M. Dollard, West Seneca; Eugene Odin, Williamsville; Donald T. Donahue, Kenmore, all of N.Y.

[73] Assignee: Buffalo Color Corporation, West Paterson, N.J.

[21] Appl. No.: 127,774

[22] Filed: Mar. 6, 1980

[51] Int. Cl.$^3$ .................. C07C 37/82; C07C 39/21
[52] U.S. Cl. .................. 568/730; 568/749; 568/758; 568/724; 568/742
[58] Field of Search ........... 568/724, 748, 742, 722, 568/723, 730, 738, 758, 749, 769, 795, 762

[56] References Cited

U.S. PATENT DOCUMENTS

| | | | |
|---|---|---|---|
| 1,988,156 | 1/1935 | Bouvier et al. | 568/738 |
| 2,247,523 | 7/1941 | Schick et al. | 568/758 |
| 2,254,745 | 9/1941 | Jannek | 568/758 |
| 2,334,488 | 11/1943 | Harris et al. | 568/795 |
| 2,368,361 | 1/1945 | Jenkins | 568/717 |
| 3,413,341 | 11/1968 | Bursack | 568/722 |
| 3,453,332 | 7/1969 | Vesely | 568/741 |
| 3,535,389 | 10/1970 | De Jong | 568/724 |
| 3,813,445 | 5/1974 | Massie | 568/730 |
| 3,965,036 | 6/1976 | Himmelstein | 568/758 |
| 4,058,457 | 11/1977 | Manes | 568/753 |
| 4,113,974 | 9/1978 | Mark | 568/750 |
| 4,169,211 | 9/1979 | Ligorati et al. | 568/724 |
| 4,243,822 | 1/1981 | Demler et al. | 568/769 |

FOREIGN PATENT DOCUMENTS

| | | | |
|---|---|---|---|
| 7204188 | 10/1973 | Netherlands | 568/749 |
| 1537835 | 1/1979 | United Kingdom | 568/749 |

*Primary Examiner*—Werren B. Lone
*Attorney, Agent, or Firm*—Michael L. Dunn

[57] ABSTRACT

A process for purifying 4,4'-dihydroxydiphenyl comprising contacting a solution of 4,4'-dihydroxydiphenyl alkali metal salt with activated carbon followed by removing the activated carbon from the solution and acidifying the solution with sufficient acid to convert essentially all of the 4,4'-dihydroxydiphenyl alkali metal salt to water insoluble 4,4'-dihydroxydiphenyl and 4,4'-dihydroxydiphenyl product containing less than 0.45 weight percent of 4-monohydroxydiphenyl impurity.

31 Claims, No Drawings

PROCESS FOR THE PURIFICATION OF 4,4' DIHYDROXYDIPHENYL

BACKGROUND OF THE INVENTION (a) Field of the Invention

This invention relates to a process for the manufacture of 4,4'-dihydroxydiphenyl (biphenol, diphenol) and more particularly relates to a process for the purification of 4,4'-dihydroxydiphenyl which contains 4-monohydroxydiphenyl impurity.

(b) History of the Prior Art

Biphenol is useful as a reactant in condensation polymerizations and is particularly useful in forming phenolic type resins having good temperature resistance.

Biphenol was formed in the prior art by various methods. For example, halogenated diphenyl could be hydrolyzed (U.S. Pat. No. 3,413,341) or diphenyl could possibly be directly hydroxylated with peroxide in the presence of a suitable catalyst (U.S. Pat. No. 3,453,332).

One of the most suitable methods for the preparation of biphenol is sulfonation of diphenyl to form diphenyldisulfonic acid which is then reacted with an alkali metal hydroxide or alkali metal salt to form a diphenyldisulfonic acid salt followed by fusion of the diphenyldisulfonic acid salt with an alkali metal hydroxide to form the sodium salt of biphenol followed by dissolving of the reaction mass and acidification to form biphenol. Such processes are described in U.S. Pat. No. 2,368,361 and copending Patent Application Ser. No. 071,572 filed Aug. 31, 1979.

In all of the prior art processes and especially in those involving fusion reaction, a significant quantity, i.e., in excess of 1%, of 4-monohydroxydiphenyl is formed. In fusion reactions, this is due to the presence of diphenylmonosulfonic acid salt which is formed during sulfonation of diphenyl and which is exceedingly difficult to remove from the desired diphenyl disulfonic acid salt. Such impurities in hydrolysis of halogenated diphenyl result from the presence of monohalogenated diphenyl products which occur during the halogenation process and which are also difficult to remove from the dihalodiphenyl compounds. Similarly, direct hydroxylation with peroxide can result in the attachment of a single OH group which will result in undesired monhydroxy impurity.

Such monohydroxydiphenyl impurity is especially significant when biphenol is formed from fusion type reactions. In the past, purification methods usually employed to purify the biphenol product have been ineffective to remove monohydroxydiphenyl. Recrystallization is ineffective since the recrystallized product also contains recrystallized monohydroxydiphenyl. Distillation is ineffective due to the close boiling temperatures of monohydroxy and dihydroxydiphenyl and sublimation is ineffective since the monohydroxydiphenyl sublimes at a temperature close to the sublimation temperature of diphyroxydiphenyl and if anything, results in an increased concentration of monohydroxydiphenyl impurities since during sublimation, there is a higher concentration of monohydroxydiphenyl during the first part of the sublimation process. The presence of monohydroxydiphenyl in the 4,4'-dihydroxydiphenyl product is believed to be undesirable since when the 4,4'-dihydroxydiphenyl is used in a polymerization, it is believed that the monohydroxydiphenyl acts a chain terminator thus preventing the formation of polymers with molecular weights which are as high as would be obtainable in the absence of the monohydroxydiphenyl impurity.

It had been previously thought that the removal of the monohydroxydiphenyl impurity was much too costly since no inexpensive standard purification means appeared to efficiently accomplish the purification.

BRIEF DESCRIPTION OF THE INVENTION

The invention is a process for purifying 4,4'-dihydroxydiphenyl which comprises contacting a solution of 4,4'-dhydroxydiphenyl alkali metal salt with activated carbon followed by removing the activated carbon from the solution and acidifying the solution with sufficient acid to convert essentially all of the 4,4'-dihydroxydiphenyl alkali metal salt to water insoluble 4,4'-dihydroxydiphenyl. The purification process results in removal of almost all of the 4-monohydroxydiphenyl impurity to obtain a product which contains less than about 0.45 weight percent 4-monohydroxydiphenyl, usually less than 0.2 weight percent, and often less than 0.1 weight percent 4-monohydroxydiphenyl impurity.

The purification process is particularly applicable to a process for the preparation of 4,4'-dihydroxydiphenyl by fusion reaction of an alkali metal hydroxide with an alkali metal diphenyl disulfonate to form the alkali metal salt of 4,4'-dihydroxydiphenyl wherein the reaction mass is contacted with sufficient water to dissolve essentially all water soluble components of the mass to form a first solution; separating the resulting solution from insolubles; acidifying the solution into a sufficiently low pH to precipitate essentially all 4,4'-dihydroxydiphenyl product and separating the precipitated product from the remaining liquid. In using the purification process, the first solution obtained by dissolving the reaction mass is contacted with activated carbon at from about 0° to about 100° C. for more than about 1 minute prior to separating the resulting solution from insolubles including the activated carbon.

Optionally, for even better purification, a second solution may be formed by dissolving the resulting precipitated product in sufficient aqueous liquid having a sufficiently high pH to cause the product to dissolve as 4,4'-dihydroxydiphenyl metal salt; contacting the resulting second solution with activated carbon at a temperature of from about 0° to about 100° C. for more than about 1 minute; separating the solution from insolubles; acidifying the second solution to a sufficiently low pH to precipitate essentially all 4,4'-dihydroxydiphenyl product; and separating the product precipitated out of the second solution from remaining liquid.

Alternatively, but not preferably, the first solution need not be contacted with activated carbon and the 4,4'-dihydroxydiphenyl product can be precipitated followed by separating the precipitated product from the remaining liquid. The precipitated product may then be redissolved in aqueous liquid having a sufficiently high pH to cause the product to dissolve and then activated carbon may be contacted with (e.g., be slurried into) the resulting second solution at a temperature of from about 0° to about 100° C. for more than about 1 minute. The insolubles may then be separated from the second solution, e.g., by filtration. The second solution may then be acidified to a sufficiently low pH to precipitate essentially all of 4,4'-dihydroxydiphenyl product and the product may be separated from the remaining liquid.

In each of the above cases, substantial quantities of monohydroxydiphenyl impurity are removed from the 4,4'-dihydroxydiphenyl desired product. It has unexpectedly been found that better removal is obtained when the activated carbon is slurried into the solution first formed by dissolving the initial reaction mass.

When 4,4'-dihydroxydiphenyl product is obtained from other processes, the product may, of course, be dissolved in sufficient aqueous liquid having a sufficiently high pH to cause the product to dissolve as 4,4'-dihydroxydiphenyl alkali metal salt followed by contacting the resulting solution with activated carbon at temperatures from about 0° to about 100° C. for more than about 1 minute. The solution may then be acidified to a sufficiently low pH to precipitate essentially all 4,4'-dihydroxydiphenyl product and a purified product may be separated from the remaining liquid.

DETAILED DESCRIPTION OF THE INVENTION

In accordance with this invention, there is provided a process which permits purification of biphenol to remove essentially all 4-monohydroxydiphenyl impurity. In particular, the method comprises contacting a solution of 4,4'-dihydroxydiphenyl alkali metal salt with activated carbon followed by removing the activated carbon from the solution and acidifying the solution with sufficient acid to convert essentially all of the 4,4'-dihydroxydiphenyl alkali metal salt to water insoluble 4,4'-dihydroxydiphenyl. Unexpectedly, activated carbon selectively removes 4-monohydroxydiphenyl alkali metal salt from the solution.

The invention is applicable to remove 4-monohydroxydiphenyl impurity from 4,4'-dihydroxydiphenyl regardless of how the 4,4'-dihydroxydiphenyl is manufactured. The 4,4'-dihydroxydiphenyl can be manufactured by hydrolysis of halogenated diphenyl or by direct hydroxylation of diphenyl with peroxide or by sulfonation of diphenyl followed by reaction with an alkali metal hydroxide to form the alkali metal salt and the fusion of the metal salt with hydroxide to form the alkali metal salt of biphenol.

"Sufficient acid" means a ratio of acid to biphenol salt plus metal hydroxide of 1:1 in unit equivalent weights.

As used herein, "convert essentially all" means that 95% conversion is obtained. "Remove essentially all" means that 4 monohydroxydiphenyl impurity is reduced in the 4,4'-dihydroxydiphenyl, to a concentration of less than about 0.45 percent by weight of final product.

"Activated carbon" means any porous carbon in granular form which has not already absorbed its capacity of organic materials. In general, the activated carbon has an average particle size between about 10 and about 75 microns and an effective surface area of from about 1000 to about 3000 square meters per gram.

Usually from about 7 to about 40 weight percent activated carbon by weight of dissolved 4,4'-dihydroxydiphenyl alkali metal salt is slurried into the solution; however, when activated carbon is used, having a large average particle size, i.e., in excess of 50 microns, larger percentages of the carbon may be used.

The 4,4'-dihydroxydiphenyl (biphenol) may be purified by dissolving the biphenol in an aqueous liquid having a sufficiently high pH to cause the product to dissolve. In general, the sufficiently high pH is above about 11.0. In general, the amount of water used to dissolve the product is from about 2 to about 20 milliliters of water per gram of reaction mass, i.e., combined biphenol salt, reactants, by products and impurities and sufficent base to obtain a sufficiently high pH. Activated carbon is slurried into the resulting solution at a temperature from about 0° to 100° C. Higher temperatures are not needed or required but may be used when the solution is under pressure to permit the aqueous solution to reach a higher temperature before boiling. Contact time of the activated carbon with the solution is generally for an excess of about 1 minute. Optimumly, the contact time is from about 1 to about 60 minutes. Longer contact times may be used; however, additional removal of monohydroxydiphenyl due to the increased contact time is found to be minimal.

After contacting the activated carbon with the solution, the activated carbon is removed by any suitable means such as filtration or centrifuging. The solution is then acidified to a sufficiently low pH to precipitate essentially all 4,4'-dihydroxydiphenyl product. The sufficiently low pH is generally from about 1 to about 10 and is preferably from about 1 to about 5. The resulting purified product is then separated from the remaining liquid. The product is generally found to contain less than 0.45 weight percent monohydroxydiphenyl impurity. The impurity, in fact, is often less than 0.2 weight percent and is sometimes 0.1 weight percent depending upon solution pH's contact time, product concentration and activated carbon specifications. Usually, the sufficiently low pH is obtained by adding any suitable inorganic acid such as hydrochloric acid, sulfuric acid, nitric acid or a phosphoric acid. The sufficiently high pH is usually obtained by adding alkali metal hydroxide such as potassium or sodium hydroxide.

When the 4,4'-dihydroxydiphenyl is prepared by fusion reaction of an alkali metal hydroxide with an alkali metal diphenyldisulfonate to form the alkali metal salt of 4,4'-dihydroxydiphenyl, followed by contacting the resulting reaction mass with sufficient water to dissolve essentially all water soluble components of the mass to form a first solution; separating the resulting solution from the insolubles; acidifying the solution to a sufficiently low pH to precipitate essentially all 4,4'-dihydroxydiphenyl product and separating the precipitated product from remaining liquid; the product may be purified by contacting the first solution with activated carbon at from about 0° to 100° C. for more than about 1 minute prior to separating the solution from insolubles.

The resulting product then generally contains less than about 0.45 weight percent of monohydroxydiphenyl impurity. The product may then be further purified by forming a second solution by dissolving the resulting precipitated product in sufficient aqueous liquid, as previously discussed, having a sufficiently high pH to cause the product to dissolve as the 4,4'-dihydroxydiphenyl alkali metal salt. The resulting second solution is then contacted with activated carbon at a temperature of from about 0° to about 100° C. for more than 1 minute and the activated carbon is removed. The second solution is then treated with an acid to obtain a sufficiently low pH to precipitate essentially all 4,4'-dihydroxydiphenyl product and the precipitated product is then separated from remaining liquid.

In accordance with the purification process of the invention, the activated carbon may be contacted with the solution by any suitable means. Examples of such means include slurrying the carbon into the solution or passing the solution through a column containing the activated carbon. All that is required is that the solution be intimately contacted with the activated carbon.

When biphenol is prepared by fusion reaction of alkali metal diphenyldisulfonate with alkali metal hydroxide, it has been unexpectedly found that better removal of monohydroxydiphenyl impurity is obtained when the dissolved reaction mass is contacted with activated carbon rather than first precipitating biphenol from the reaction mass and then redissolving the biphenol in a second solution which is contacted with the activated carbon. Desirably, the first solution formed by dissolving the reaction mass is contacted with activated carbon up to about 15 and most preferably up to about 60 minutes.

The following examples serve to illustrate and not limit the present invention:

EXAMPLE 1

3000 grams of potassium hydroxide flakes (90% KOH) are melted at from about 230° to about 250° C. 2000 grams of dipotassium diphenyldisulfonic acid are then slowly added to the melted potassium hydroxide and the mixture is heated to from about 335° to 340° C. After three hours, the temperature is increased to 360° C. and the reaction mixture is poured into a stainless steel pan to cool. After the reaction mass is solidified, it is broken up. 200 grams of the reaction mass is dissolved in 500 milliliters of hot water. The solution is filtered through a flock bed and washed with 50 milliliters of additional hot water. 190 milliliters of 36% HCl is added to the solution to adjust the pH to 1.7 and the solution is agitated for 1 hour at from 90° to 95° C. The resulting insoluble product is separated by filtration at 90° C. and washed with 1000 milliliters of hot distilled water. The product is then dried under a vacuum at 100° C. An analysis of the resulting product is set forth in Table I.

EXAMPLE 2

Example 1 is repeated except that 7.73 grams of activated carbon having a surface area of from about 1400 to 1800 square meters per gram and an average particle size of smaller than 44 microns with about 15% of the particles having a particle size larger than 74 microns was added to the solution of the fusion mass in water. The activated carbon used is 20% by weight based on the theoretical amount of biphenol present. The mixture of the activated carbon and solution is held at 70° C. for 30 minutes before it is filtered through a flock bed. The analysis of the resulting product is shown in Table I.

EXAMPLE 3

Example 1 is repeated except that the resulting product is not dried. It is slurried into 500 milliliters of hot water and 22 milliliters of 50% sodium hydroxide solution is added to dissolve the product. 7.73 grams of activated carbon, as previously described, is added to the solution and agitated at 70° C. for ½ hour. The solution is then filtered through a flock bed. The analysis of the resulting product is shown in Table I.

TABLE I

| Example | % Strength | % Monohydroxy | ASH | Melting Point °C. | Na | Ca | K |
|---|---|---|---|---|---|---|---|
| 1 | 97.1 | 1.6 | 0.34 | 279.5 | 67 | 24 | 1283 |
| 2 | 100.3 | 0.16 | 0.33 | 279.2 | 54 | 47 | 838 |
| 3 | 102.2 | 0.42 | 0.09 | 282.2 | 70 | 29 | 81 |

A comparison of the foregoing examples illustrates that the use of activated carbon is exceedingly effective in removing monohydroxydiphenyl impurity. A comparison of the examples also show that the most effective removal is obtained when the fusion reaction mass is dissolved and treated without previously precipitating the biphenol product (Example 2). But some removal is obtained whenever the activated carbon is used (Example 3).

Even better results are obtained when the product, as prepared in Example 2, is redissolved and retreated with activated carbon. In such cases, the monohydroxydiphenyl present is usually less than 0.1 weight percent. Low percentages i.e., less than 0.1 weight percent, can also be obtained with large quantities of activated carbon, e.g., over 30% by weight of biphenol, which will be theoretically obtained in the manner described in Example 2.

What is claimed is:

1. A process for purifying 4,4'-dihydroxydiphenyl comprising contacting a solution of 4,4'-dihydroxydiphenyl containing 4-monohydroxydiphenyl alkali metal salt with activated carbon followed by removing the activated carbon from the solution and acidifying the solution with sufficient acid to convert essentially all of the 4,4'-dihydroxydiphenyl alkali metal salt to water insoluble 4,4'-dihydroxydiphenyl.

2. In a process for the preparation of 4,4'-dihydroxydiphenyl by:
   (a) fusion reaction of an alkali metal hydroxide with an alkali metal diphenyl disulfonate to form the alkali metal salt of 4,4'-dihydroxydiphenyl;
   (b) contacting the resulting reaction mass with sufficient water to dissolve essentially all water soluble components of the mass to form a first solution;
   (c) separating the resulting solution from insolubles;
   (d) acidifying the solution to a sufficiently low pH to precipitate essentially all 4,4'-dihydroxydiphenyl product; and
   (e) separating the precipitated product from remaining liquid;

the improvement which comprises:
   (f) contacting the first solution with activated carbon at from about 0° to about 100° C. for more than about 1 minute prior to separating the resulting solution from insolubles.

3. The process of claim 2 wherein the improvement further comprises:
   (g) forming a second solution by dissolving the resulting precipitated product in sufficient aqueous liquid having a sufficiently high pH to cause the product to dissolve as 4,4'-dihydroxydiphenyl alkali metal salt;
   (h) contacting the resulting second solution with activated carbon at a temperature of from about 0° to about 100° C. for more than about one minute;
   (i) removing the activated carbon from the solution;
   (j) acidifying the second solution to a sufficiently low pH to precipitate essentially all 4,4'-dihydroxydiphenyl product; and
   (k) separating the product precipitated out of the second solution from remaining liquid.

4. A process for the purification of 4,4'-dihydroxydiphenyl by:
  (a) forming a solution by dissolving the 4,4'-dihydroxydiphenyl in an aqueous liquid having a sufficiently high pH to cause the product to dissolve;
  (b) slurrying activated carbon into the resulting solution at a temperature of from about 0° to about 100° C. for more than about 1 minute;
  (c) removing the activated carbon from the solution;
  (d) acidifying the solution to a sufficiently low pH to precipitate essentially all 4,4'-dihydroxydiphenyl product; and
  (e) separating the resulting product from remaining liquid.

5. The process of claim 2 wherein the first solution is contacted with activated carbon for up to 60 minutes.

6. The process of claim 2 wherein the first solution is contacted with activated carbon for up to 15 minutes.

7. The process of claim 2 wherein the reaction mass is contacted with water at a temperature of from 0° to about 100° C.

8. The process of claim 7 wherein the water used to dissolve the reaction mass is from about 2 to 20 milliliters of water per gram of reaction mass.

9. The process of claim 7 wherein the water used to dissolve the reaction mass is from about 2 to about 4 milliliters of water per gram of reaction mass.

10. The process of claim 3 wherein the reaction mass is contacted with water at a temperature of from 0° to about 100° C. at atmospheric pressure.

11. The process of claim 4 wherein the reaction mass is contacted with water at a temperature of from 0° to about 100° C. at atmospheric pressure.

12. The process of claim 2 wherein, in step (c), the resulting solution is separated from insolubles by means of filtration.

13. The process of claim 3 wherein, in step (c), the resulting solution is separated from insolubles by means of filtration.

14. The process of claim 4 wherein, in step (c), the resulting solution is separated from activated carbon by means of filtration.

15. The process of claim 5 wherein, in step (c), the resulting solution is separated from insolubles by means of filtration.

16. The process of claim 7 wherein, in step (c), the resulting solution is separated from insolubles by means of filtration.

17. The process of claim 2 wherein the sufficiently low pH in step (d) is below 10.

18. The process of claim 3 wherein the sufficiently low pH in step (d) is from about 1 to about 10 and the sufficiently high pH in step (g) is above 11.0.

19. The process of claim 4 wherein the sufficiently low pH in step (d) is from about 1 to about 10 and the sufficiently high pH in step (a) is above 11.0.

20. The process of claim 2 wherein, in step (e), the precipitated product is separated by filtration.

21. The process of claim 2 wherein the first solution is contacted with activated carbon by slurrying from 7 to about 40 weight percent activated carbon, by weight of dissolved alkali metal salt of 4,4'-dihydroxydiphenyl, into the first solution.

22. The process of claim 3 wherein both the first solution in step (f) and the second solution in step (h) are contacted with activated carbon by slurrying from about 7 to about 40 weight percent activated carbon, by weight of dissolved 4,4'-dihydroxydiphenyl alkali metal salt, into the first and second solutions.

23. The process of claim 4 wherein the second solution is contacted with activated carbon by slurrying from about 7 to about 40 weight percent activated carbon, by weight of dissolved 4,4'-dihydroxydiphenyl alkali metal salt, into the second solution.

24. The process of claim 2 wherein the activated carbon has an average particle size of between about 10 and about 75 microns and an effective surface area of from about 1000 to about 3000 square meters per gram.

25. The process of claim 3 wherein the activated carbon has an average particle size of between about 10 and about 75 microns and an effective surface area of from about 1000 to about 3000 square meters per gram.

26. The process of claim 4 wherein the activated carbon has an average particle size of between about 10 and about 75 microns and an effective surface area of from about 1000 to about 3000 square meters per gram.

27. The process of claim 5 wherein the activated carbon has an average particle size of between about 10 and about 75 microns and an effective surface area of from about 1000 to about 3000 square meters per gram.

28. The process of claim 6 wherein the activated carbon has an average particle size of between about 10 and about 75 microns and an effective surface area of from about 1000 to about 3000 square meters per gram.

29. The process of claim 21 wherein the activated carbon has an average particle size of between about 10 and about 75 microns and an effective surface area of from about 1000 to about 3000 square meters per gram.

30. The process of claim 22 wherein the activated carbon has an average particle size of between about 10 and about 75 microns and an effective surface area of from about 1000 to about 3000 square meters per gram.

31. The process of claim 23 wherein the activated carbon has an average particle size of between about 10 and about 75 microns and an effective surface area of from about 1000 to about 3000 square meters per gram.

* * * * *